United States Patent [19]

Oshima

[11] 4,141,939
[45] Feb. 27, 1979

[54] AERATOR FOR GENERATING FINE BUBBLES BY SUPERSONIC WAVE ACTION

[76] Inventor: Hikoji Oshima, 3474-1, Nishionuma, Sagamihara-shi Kanagawa-ken, Japan, 229

[21] Appl. No.: 805,430

[22] Filed: Jun. 10, 1977

[51] Int. Cl.² .............................................. B05B 1/10
[52] U.S. Cl. ........................................ 261/1; 239/102; 261/76; 261/DIG. 48; 261/DIG. 78
[58] Field of Search ............. 261/1, 76, 124, DIG. 48, 261/DIG. 78; 239/102, 431; 128/DIG. 2

[56] References Cited

U.S. PATENT DOCUMENTS

| | | | |
|---|---|---|---|
| 1,747,687 | 2/1930 | Wheeler | 261/124 |
| 2,532,554 | 12/1950 | Joeck | 261/1 |
| 3,157,359 | 11/1964 | Fortman | 239/102 |
| 3,240,253 | 3/1966 | Hughes | 239/102 |
| 3,326,467 | 6/1967 | Fortman | 261/DIG. 48 |
| 3,409,274 | 11/1968 | Lawton | 261/76 |
| 3,494,099 | 2/1970 | Eng et al. | 261/DIG. 48 |
| 3,545,947 | 12/1970 | Gray et al. | 261/1 |
| 3,746,257 | 7/1973 | Broad et al. | 239/102 |
| 3,758,033 | 9/1973 | Schurig et al. | 239/102 |

FOREIGN PATENT DOCUMENTS

971536  1/1951  France .................................. 261/76

Primary Examiner—Bernard Nozick
Assistant Examiner—Gregory N. Clements
Attorney, Agent, or Firm—James A. Wong

[57] ABSTRACT

This invention is directed to an aerator device and method for generating fine bubbles from a liquid and gas mixture. In particular this invention is directed to aeration of liquid to generate fine bubbles for industrial as well as for domestic use.

1 Claim, 2 Drawing Figures

4,141,939

AERATOR FOR GENERATING FINE BUBBLES BY SUPERSONIC WAVE ACTION

BACKGROUND OF THE INVENTION

Heretofore the production of liquid bubbles has been achieved by various known methods including mechanically stirring or agitating the liquid surface, ejection of air into the liquid, and suction of air into the liquid by a reduced pressure action by ejecting liquid at high velocity.

In recent developments these aeration methods have been favorably regarded for use in a gas-liquid contact device or for an aeration device, but were not fully satisfactory from the point of efficiency, e.g., available data showed that the practical use of known aeration devices amounted to only about 9% of the total oxygen output.

Consequently, applicant conducted extensive research to produce a more effective aeration device and as a result has discovered that supersonic wave is generated when liquid is ejected at high velocity and air is mixed into the motive fluid flow to form bubbles, and successfully reduced this invention to practice by effectively utilizing supersonic wave.

With the foregoing in mind, one object of this invention is to provide an aeration device capable of forming fine bubbles using supersonic wave action.

Another object of this invention is to provide an aeration device that effectively produces an aerated motive fluid flow adaptable to a wide range of uses.

A further object of this invention is to provide warming, vibrating and germicidal actions by effectively producing an air-liquid contact.

It is yet another object of this invention to effect sterilization by water treatment of active sludge by supersonic wave action.

It is moreover an object of this invention to effect motive fluid flow by supersonic wave action for use in washing with water.

It is furthermore an object of this invention to supply water for a warm bath, face washing, or massage by supersonic wave action.

Other objects, benefits, and advantages of this invention will be readily appreciated upon reading the remainder of this specification and considering the structure illustrated in the accompanying drawing.

SUMMARY OF THE INVENTION

With the foregoing in mind the reader will readily appreciate the concept of the instant invention which utilizes supersonic wave action developed in a liquid when bubbles are generated in an apparatus and are destroyed or crushed as the bubbles collide or dash against wall portions of the apparatus. It will be clear that according to the present invention fine bubbles are produced in motive fluid flow with a supersonic wave atmosphere in an aerator. While the basis for the development of the foregoing is not entirely clear, stepped up activity of molecular movement between liquid and air due to supersonic wave action or reduction in surface tension of the liquid as a result of supersonic wave vibration are offered as possible explanation of the phenomenon. Also, as supersonic wave is known to produce excitation of the molecules, and contact establishes an excited condition when the present invention is used as an air-liquid contact device, especially an air-liquid contact device in which a small amount of air is brought into contact with the liquid, or by using it as an aeration device. Therefore, in addition to providing an improved contact frequency, the present invention also improves effectiveness by supersonic wave. Moreover, as supersonic wave possesses warming, cleansing, vibrating and germicidal actions, the present invention develops these characteristics in the sterilization of liquid, for example, in an effective sterilization treatment of activated sludge. Further, the present invention may be effectively used for cleansing action by spurting or jetting the cleaning fluid. Still another use of the present invention is its use in effectively warming, washing, and massaging and bathing the human body.

Additional advantages of the present invention reside in the simplicity of the structure of the aerator, and its ability to effect a jet or spurt without wasting large amounts of water which considerably broadens the range of industrial use. Also, this invention makes it possible to produce fine bubbles by providing a lower $\Delta P$ or pressure differential as compared to the known methods of subdividing the formed bubbles with a filter.

DETAILED DESCRIPTION OF THE INVENTION

Figure 1:
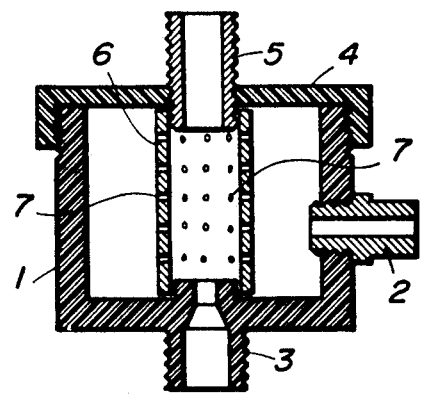
FIG. 1 represents a mid-sectional view taken along a vertical plane of an aerator apparatus according to a first embodiment of the present invention.

Referring now in detail to the drawings and with particular attention to FIG. 1, the reader will readily appreciate that an aerator apparatus is illustrated with a casing 1; having an air inlet or vent 2 shown to be in the form of a tube; a nozzle 3 through which motive liquid may be introduced; a lid 4 secured at the top of casing 1; and outlet 5; and a body 6 defining cavity or chamber 16 with a plurality of pores 7 in the wall of resonating body 6. As may be clearly seen in FIG. 1, an aerator apparatus according to the present invention comprises a casing 1 with nozzle 3 for liquid at the bottom of casing 1 and fluid outlet 5 for aerated motive fluid flow disposed at the top of lid 4. Resonant body 6 is seen to extend between nozzle 3 and fluid outlet 5 to provide a passage therebetween. Resonant body 6 is further seen to be located generally centrally of the interior of casing 1 at a substantial space away from the wall of casing 1. Resonant body 6 is further seen to extend in surrounding relationship around the outlet end of nozzle 3 and the inner end of outlet 5. Air inlet vent 2 extends through a side wall portion of casing 1 whereby air may be introduced into the casing 1 in the space around resonant body 6.

Use of the aerator apparatus of FIG. 1 is achieved by introducing liquid through nozzle 3 which is effused from nozzle 3 into resonating cavity or chamber 16, while at the same time air inlet allows air to be drawn into casing 1 from the atmosphere or an air chamber which may be built and/or mounted on casing 1. As a plurality of pores 7 are seen to extend transversely through the wall of resonant chamber 6, it is clear that as motive fluid is effused from nozzle 3 into resonant chamber 16 air introduced into casing 1 through inlet vent 2 will naturally be drawn into chamber 16 through pores 7 to form bubbles by mixing with the motive fluid in resonant chamber 16 to produce aerated liquid which is then ejected from casing 1 through outlet 5 with fine bubbles in a spurt or jet. The numerous pores 7 as illustrated in FIG. 1 are to be understood to extend through the wall of resonant body 6 in a circumferential pattern along the entire length thereof.

Figure 2:
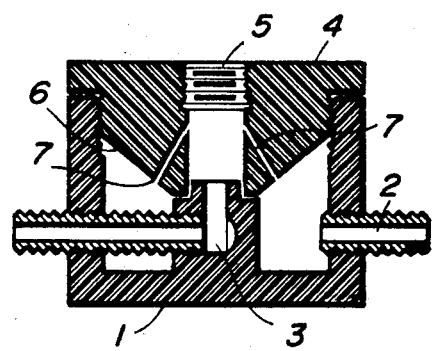
FIG. 2 represents a view similar to FIG. 1 of an alternative embodiment of the present invention.

The alternative embodiment of the present invention illustrated in FIG. 2 comprises lid 4 and the resonant body 6 as an integral member with the lower part of the resonant body 6 formed as a taper surface, and the numerous pores 7 each connected in series to a hollow part of the tube's taper surface. The resonant body 6, however, may be constructed with a smaller diameter than the inner circumference of the casing 1 which is quite different from the structure illustrated in FIG. 2 and may be suspended from lid 4. The pores 7 are open at opposite ends thereof and extend at a fixed angle to the axis of the resonant cavity 16 and as seen in FIG. 2 to be oblique, in contrast to the pores 7 in the embodiment of FIG. 1 in which such pores 7 are perpendicular to the axis of the resonant cavity 16. The frequency or number of cycles of the supersonic wave generated by the aerator of FIG. 2 may be altered by altering the angle of pores 7. The diameter of these pores 7 may be suitably designed to produce a desired range of supersonic wave together with the ejection speed of the liquid. Further, according to the embodiment of aerator illustrated in FIG. 2, when the liquid flow from nozzle 3 is ejected toward the outlet 5 within the resonant cavity 16, a reduction in the pressure occurs in the numerous pores 7 due to the effusion of the liquid flow and air is sucked within the resonant cavity 16 by way of pores 7 from air inlet 2. Thus, this air forms bubbles by being mixed within the ejected motive fluid flow and produce aerated motive fluid flow and the aerated current jets out from outlet 5. Also, when the air mixes with the motive fluid flow through the pores 7, the air current becomes turbulent and each of the pores 7 in the wall of resonant body 6, as well as the resonant cavity 16 itself, becomes a resonant cavity and generates supersonic wave, and forms bubbles under supersonic wave atmosphere. Even though no mention has been made on the experimental production of resonant body 6 using synthetic resin and metal, the former produced less supersonic wave, while the latter generated many times the number of high frequency waves; the latter generated supersonic wave by the resonant action with said resonant body 6 and it is evident that the harder the material for the resonant body 6, the greater the advantage. The resonant body 6 illustrated in FIG. 2 includes a generally cylindrical inner or cavity surface and a conical or tapered outer surface, which diverges in the direction from nozzle 3 toward outlet 5 so that different flow patterns and mixing characteristics from that of the embodiment of FIG. 1 may be obtained. In addition, there was some difference in the generation of supersonic wave depending on the material used for the casing 1, but effective supersonic wave can be generated by building the entire casing 1 or only the inner surface thereof with hard material such as metal due to the deflection and absorption of the supersonic waves. The aerator of this invention produces fine bubbles since bubbles are formed in the motive fluid flow with supersonic wave atmosphere as explained above. While the principle of the invention is not completely clear, it is believed that the activation of the molecular movement between the liquid and the air due to the supersonic wave vibration, or due to the reduction in surface tension of the liquid owing to the supersonic wave vibration is the basis thereof.

While the invention has been described with reference to particular embodiments thereof, it is to be understood that modifications may be made by persons skilled in the art without departing from the spirit of the invention or from the scope of the invention defined in the appended claims.

What is claimed is:

1. An aerator apparatus for generating fine bubbles from a mixture of liquid and gas comprising:
    (a) a casing including a bottom portion with an enclosure forming wall portion extending upwardly therefrom, a lid member disposed on top of said wall;
    (b) inlet means extending through said casing for admission of air into said casing from a source externally thereof;
    (c) nozzle means for introducing liquid into said casing, said nozzle means including an exit disposed inside of said casing and an inlet passage extending from outside of said casing, through said casing and in communication with said exit;
    (d) means defining a resonant cavity or chamber disposed internally of said casing in spaced-apart nozzle means with the exit of said nozzle means in position to introduce liquid into said resonant cavity or chamber;
    (e) outlet means extending through said casing through which fluid may be discharged or ejected from said casing, said outlet means being in alignment with said resonant cavity or chamber and said nozzle means, said outlet means also being at a downstream end of said resonant cavity or chamber opposite from nozzle means; and
    (f) a plurality of pores extending through said means defining resonant cavity or chamber whereby as motive liquid is effused through said nozzle means into said resonant cavity or chamber, air admitted into said casing through said inlet means will be drawn into said resonant cavity or chamber through said plurality of pores and will mix with liquid to form bubbles thereby producing aerated liquid which is thereafter ejected through said outlet means in a spurt or jet, wherein said means defining said resonant cavity or chamber is formed with a tapered outer surface diverging from said nozzle means in the direction toward said lid member and a generally cylindrical inner surface, and said plurality of pores extend obliquely through said means defining said resonant cavity or chamber.

* * * * *